United States Patent
Anelli et al.

(10) Patent No.: US 7,244,864 B2
(45) Date of Patent: Jul. 17, 2007

(54) PROCESS FOR THE PREPARATION OF N,N-SUBSTITUTED 5-AMINO-1,3-BENZENEDICARBOXAMIDES

(75) Inventors: Pier Lucio Anelli, Milan (IT); Marino Brocchetta, Milan (IT); Giovanna Lux, Milan (IT); Enrico Cappelletti, Milan (IT)

(73) Assignee: Bracco Imaging S.p.A., Milan (IT)

( * ) Notice: Subject to any disclaimer, the term of this patent is extended or adjusted under 35 U.S.C. 154(b) by 384 days.

(21) Appl. No.: 10/433,388

(22) PCT Filed: Nov. 28, 2001

(86) PCT No.: PCT/EP01/13879

§ 371 (c)(1),
(2), (4) Date: Dec. 22, 2003

(87) PCT Pub. No.: WO02/44125

PCT Pub. Date: Jun. 6, 2002

(65) Prior Publication Data

US 2004/0082811 A1    Apr. 29, 2004

(30) Foreign Application Priority Data

Dec. 1, 2000  (IT) .......................... MI2000A2600

(51) Int. Cl.
*C07C 231/02*  (2006.01)

(52) U.S. Cl. .......... 564/134; 564/153; 560/20; 560/43

(58) Field of Classification Search ............. 564/134, 564/153; 560/20, 43

See application file for complete search history.

(56) References Cited

U.S. PATENT DOCUMENTS 4,250,113 A    2/1981   Nordal et al. ............... 564/153

FOREIGN PATENT DOCUMENTS

JP   10-251211   * 9/1998
WO   W0 00/29372   5/2000

OTHER PUBLICATIONS

PCT International Search Report for PCT/EP01/13879 dated Apr. 3, 2002.
PCT International Preliminary Examination Report for PCT/EP01/13879 dated Feb. 20, 2003.

* cited by examiner

*Primary Examiner*—Shailendra Kumar
(74) *Attorney, Agent, or Firm*—Kramer Levin Naftalis & Frankel LLP

(57) ABSTRACT

The invention relates to a process for the preparation of a compound of formula (I), wherein R represents a 2,3-dihydroxy-1-propyl or a 1,3-dihydroxy-2-propyl radical, via direct amidation of a dialkyl ester of 5-amino-1,3-benzene-dicarboxylic acid of formula (V), wherein $R_1$ represents a straight or branched $(C_1-C_4)$-alkyl group, with at least the stoichiometric amount of an amine of formula $H_2NR$.

15 Claims, No Drawings

PROCESS FOR THE PREPARATION OF N,N-SUBSTITUTED 5-AMINO-1,3-BENZENEDICARBOXAMIDES

This application is the national stage filing of corresponding international application number PCT/EP01/13879, filed Nov. 28, 2001, which claims priority of Italian application MI2000A002600, filed Dec. 1, 2000.

The present invention relates to a new process for the preparation of N,N'-substituted 5-amino-1,3-benzenedicarboxamides of formula (I),

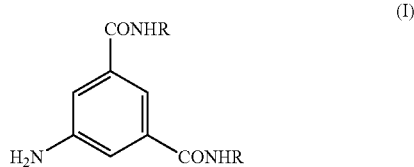

(I)

wherein R represents a 2,3-dihydroxy-1-propyl or a 1,3-dihydroxy-2-propyl group.

Compounds (I) are useful as intermediates in the preparation of X-rays contrast agents such as iopamidol (R=—CH(CH$_2$OH)$_2$) and iohexol or ioversol (R=—CH$_2$—CH(OH)—CH$_2$OH).

BACKGROUND OF THE INVENTION

Compounds (I) above are known as key intermediates in the synthesis of iodinated contrast agents.

U.S. Pat. No. 4,001,323 for instance describes a process for the preparation of iopamidol (II)

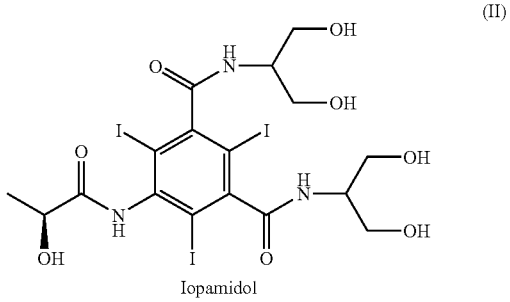

(II)

Iopamidol by iodination of a compound (I) wherein R is a group —CH(CH$_2$OH)$_2$, followed by acylation of the 5-amino group by a suitably selected chiral acylating agent.

U.S. Pat. No. 4,250,113 on the other hand discloses a similar process for the preparation of iohexol (III),

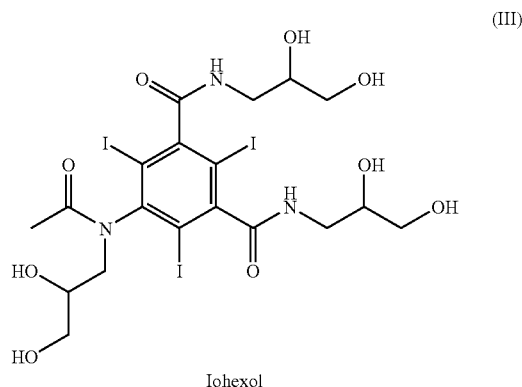

(III)

Iohexol by iodination of a compound (I) wherein R is —CH$_2$—CH(OH)—CH$_2$OH, acetylation of the 5-amino group, and N-alkylation of the resulting 5-acetamido group to yield the compound (III).

In the literature the compounds of formula (I) above are prepared starting from 5-nitro-1,3-benzenedicarboxylic acid dimethyl ester,

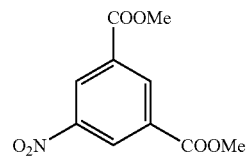

by amidation of the ester groups with 2-amino-1,3-dihydroxypropane (a compound of formula H$_2$N—CH(CH$_2$OH)$_2$ commonly known as serinol) or with 1-amino-2,3-dihydroxypropane (of formula H$_2$N—CH$_2$—CHOH—CH$_2$OH commonly known as isoserinol), followed by reduction of the 5-nitro group of the thus obtained N,N'-bis-substituted 5-nitro-1,3-benzenedicarboxamides (IV),

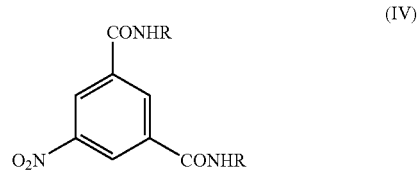

(IV)

wherein R is as defined above, to 5-amino to yield the desired products (I).

The amidation reaction in said processes is typically carried out with at least the stoichiometric amounts of serinol or isoserinol (i.e. at least two moles of serinol or isoserinol per mol of 5-nitro-1,3-benzenedicarboxylic acid dimethyl ester), in the presence of a protic organic solvent, such as a lower alkanol, and at a temperature of from about 65° C. to about 150° C.

The intermediate product (IV) is then isolated and hydrogenated in the presence of a suitable hydrogenation catalyst, such as Pd/C to yield the product (I).

An improvement to the above general method has recently been described, in WO 00/29372. The method there described involves carrying out the amidation reaction on the 5-nitro-1,3-benzenedicarboxylic acid lower alkyl esters in an organic solvent, typically a lower aliphatic alcohol, in the presence of a strong basic catalyst and then, without isolating the intermediate N,N'-substituted-5-nitro-1,3-benzenedicarboxamide (IV), catalytically hydrogenating the reaction solution to get the desired product (I). Also in this case the temperature reported for the amidation of the 5-nitro derivative is from about 65° C. to 150° C., depending on the type of solvent employed.

It has however been found that the products obtained through amidation of the 5-nitro-1,3-benzenedicarboxylic acid alkyl esters with 2-amino-1,3-dihydroxypropane or with 1-amino-2,3-dihydroxypropane, i.e. the compounds of formula (IV), are products that must be handled with great care, for their characteristic instability. Specific differential scanning calorimetry (DSC) tests have in fact demonstrated that these compounds are not stable at high temperatures even if maintained in solution. More particularly said DSC tests have shown that brought at a temperature of 120° C. the compounds of formula (IV) start decomposing with the emission of fumes. The poor stability of the 5-nitro 1,3-benzenedicarboxamides (IV) at high temperatures may drastically limit the choice of the reaction conditions that need to be strictly controlled particularly on industrial scale to prevent possible safety and pollution problems. It may also negatively affect the yields theoretically obtainable in the overall process.

There is therefore a need for an improved process that might allow to obtain the intermediate compounds (I) with high yields under reaction conditions that are easily applicable in an industrial process and where no stability problems may arise.

The process according to the present invention meets said need.

It has been found, in fact, that it is possible to obtain a compound of formula (I) in high yields also by direct amidation of a dialkyl ester of 5-amino-1,3-benzenedicarboxylic acid and that no stability problems do arise in connection with the dialkyl ester of 5-amino-1,3-benzenedicarboxylic acid or with the 5-amino-N,N'-bis-substituted-1,3-benzenecarboxamides (I) thus allowing the reaction to be carried out industrially under widely varying conditions.

SUMMARY OF THE INVENTION

A first object of the present invention is therefore a process for the preparation of a compound of formula (I),

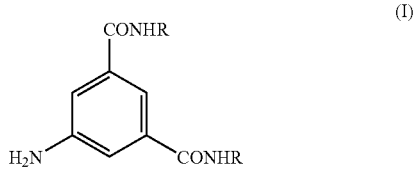

(I)

wherein R represents a 2,3-dihydroxy-1-propyl or a 1,3-dihydroxy-2-propyl radical, via direct amidation of a dialkyl ester of 5-amino-1,3-benzenedicarboxylic acid of formula (V),

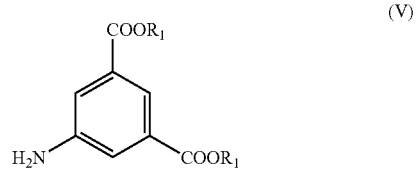

(V)

wherein $R_1$ represents a straight or branched $(C_1-C_4)$-alkyl group, with an at least stoichiometric amount of an amine of formula $H_2NR$ wherein R is as defined above.

Preferably, $R_1$ is selected from the straight $(C_1-C_4)$-alkyl groups, i.e. methyl, ethyl, n-propyl, and n-butyl. In a most preferred embodiment $R_1$ represents a n-butyl group. While the two $R_1$ groups are generally identical, as the starting compounds of formula (V) where both $R_1$ have the same meaning are more easily available, in principle they might also be different, e.g. each one may be independently selected from the group of straight or branched $(C_1-C_4)$-alkyls.

The amidation reaction according to the present invention can be carried out either in the presence of an organic solvent or in the absence of an organic solvent, i.e. as a mass reaction in the molten state using the excess of 2-amino-1,3-dihydroxypropane or 1-amino-2,3-dihydroxypropane in the molten state as the reaction medium.

When the reaction is carried out in the absence of a separate organic solvent, the excess of 2-amino-1,3-dihydroxypropane or 1-amino-2,3-dihydroxypropane is typically of at least 50% with respect to the stoichiometric amount and the reaction is carried out at a temperature above the melting temperature of 2-amino-1,3-dihydroxypropane or 1-amino-2,3-dihydroxy-propane, respectively. Typically the reaction in such a case is carried out at a temperature over 100° C., generally at a temperature of from 100° C. to 150° C., preferably comprised between 100° C. and 130° C. No problems of stability do arise as the compounds of formula (I) as well the starting 5-amino-1,3-benzenedicarboxylic acid esters (V) proved to be perfectly stable at temperatures as high as 150° C.

If a separate organic solvent is used, this is generally selected from $C_1-C_6$ straight or branched alkanols, $C_1-C_4$ straight or branched alkoxy-$C_2-C_4$ straight or branched alkanols, $C_1-C_4$ straight or branched alkyl ethers and dipolar aprotic organic solvents. Particularly preferred organic solvents in this case are $C_1-C_4$ straight alkanols, e.g. methyl alcohol, ethyl alcohol, n-propyl alcohol, and n-butyl alcohol, $C_1-C_4$ straight alkoxy-$C_2-C_4$ straight alkanols, e.g. 2-methoxyethanol, 2-ethoxyethanol, and 3-methoxypropanol, $C_1-C_4$ straight or branched alkyl ethers, e.g. ethyl ether, propyl ether, and 1,2-dimethoxyethane, N,N-dimethylacetamide, N,N-dimethylformamide, N-methyl-2-pyrrolidone, and the like solvents. The reaction is anyway preferably carried out in the presence of at least a slight excess of 1-amino-2,3-dihydroxypropane or 2-amino-1,3-dihydroxypropane, typically of from about 5 to about 20% by mol with respect to the stoichiometric amount.

In a most preferred embodiment said amidation reaction is carried out in the presence of a strong basic catalyst such as an alkali metal alcoholate, typically an alkali metal $C_1-C_4$ straight or branched aliphatic alcoholate such as sodium methylate, sodium ethylate, potassium tert-butylate, and the like basic catalysts. It has been shown in fact that unexpectedly no side reactions of the 5-amino group do occur even in the presence of a strong basic catalyst and that the amidation reaction proceeds with almost quantitative yields.

The catalyst may be added as such to the reaction mixture or it can be generated in situ, by the addition of the alkali metal to a reaction mixture where the suitably selected solvent is the corresponding alcohol (or by the addition of the alkali metal to the alcohol that will then be used as the reaction solvent). Other strong basic catalysts might be employed, such as for instance sodium or potassium hydroxides, but the water that would form in these cases should preferably be removed before the reaction, e.g. by azeotropic distillation, to avoid hydrolysis of the starting esters (V).

As indicated above, the reaction can be carried out at a temperature of from about 65° C. to about 150° C. without any problem of stability of the starting materials or of the obtained products.

When the reaction is completed, generally within a few hours, e.g. 1 to 4 hours, the desired product (I) can be isolated by conventional crystallization procedures and further processed according to any of the methods known in the literature that involve the use of such an intermediate to give the desired contrast agents, such as iopamidol, iohexol, ioversol or iomeprol.

On the other hand the excess of 1-amino-2,3-dihydroxypropane or 2-amino-1,3-dihydroxypropane used in the amidation reaction may be recovered—if desired—from the mother liquors of the crystallisation of the desired products (I), by e.g. suitably concentrating them, passing said concentrate on a cationic exchange resin, and eluting the fixed product with an ammonia solution. Recovery from this solution and purification of these products may then be carried out as described for instance in U.S. Pat. No. 5,866,719 or U.S. Pat. No. 6,111,142.

The starting compounds of formula (V) may be commercially available or they may be prepared by either reduction of the corresponding 5-nitro-1,3-benzenedicarboxylic acid alkyl esters or esterification of 5-amino-1,3-benzenedicarboxylic acid.

In one embodiment of the process according to the present invention the starting compounds of formula (V) are prepared from the corresponding 5-nitro-1,3,-benzenedicarboxylic acid diesters (VI),

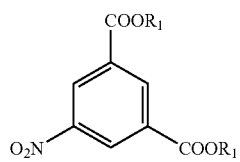
(VI)

wherein $R_1$ has the same meaning as above, by reduction of the 5-nitro group to amino.

Any of the methods known in the literature to reduce an aromatic nitro group to amino can be employed, for example chemical reduction with acids and metals, such as Zn, Sn or Fe in acidic conditions, or preferably catalytic hydrogenation with molecular hydrogen and e.g. Pd, Pt, typically supported on carbon, or Ni Ramey as the hydrogenation catalyst. A preferred catalyst is however Pd/C where Pd amounts to from about 5 to about 10% by weight of the catalyst. Catalytic hydrogenation is generally carried out at atmospheric pressure, and at a temperature comprised between about 15° C. and about 70° C. It is carried out in the presence of an organic solvent, such as $C_1$-$C_6$ straight or branched alkanols, $C_1$-$C_4$ straight or branched alkoxy-$C_2$-$C_4$ straight or branched alkanols, $C_1$-$C_4$ straight or branched alkyl ethers, or any other inert organic solvent. Optionally an amount of acid, such as hydrochloric acid, of from 0.1÷2 mol per mol of reactant can be present.

The completion time for this hydrogenation reaction is generally comprised between 0.5 and 6 hours. At the end of the reaction the catalyst is recovered by filtration and, if desired, it can be recycled. The reduced product of formula (V) can then be isolated from the filtered solution by bringing the pH to a value of from about 7.5 to about 10 and recovering the precipitate by filtration. It is however not necessary to isolate the compound of formula (V) from the solution as it is possible to carry out the amidation reaction directly thereon. In such a case, if the amidation is carried out according to the preferred embodiment that involves the use of a strong basic catalyst and the catalytic hydrogenation was carried out in acidic conditions, then it will be necessary first to remove any water possibly present by e.g. azeotropic distillation and then employ a larger amount of the basic catalyst as part of it will be used to neutralise the acid present in the reaction mixture. If isolation of the compound of formula (V) is not carried out, then the solvent employed for the catalytic hydrogenation reaction will be preferably a $C_1$-$C_6$ straight or branched alkanol, or a $C_1$-$C_4$ straight or branched alkoxy-$C_2$-$C_4$ straight or branched alkanol and even more preferably a $C_1$-$C_4$ straight alkanol, or a $C_1$-$C_4$ straight alkoxy-$C_2$-$C_4$ straight alkanol.

In their turn the compounds of formula (VI) may be commercially available or can be easily prepared according to known methods, e.g. by esterification of the 5-nitro-1,3-benzenedicarboxylic acids.

In another embodiment of the present invention the starting compounds of formula (V) are prepared by esterification of 5-amino-1,3-benzenedicarboxylic acid with the corresponding alcohol $R^1OH$, typically used as the reaction solvent, in the presence of an acidic catalyst, e.g. p-toluenesulphonic acid. The reaction quickly and easily proceeds by removing the water that forms in the esterification by e.g. azeotropic distillation. Also in this case it is not necessary to isolate the compounds of formula (V) as the amidation reaction can be carried out directly on the reaction mixture by using a larger amount of the strong basic catalyst.

As indicated above the product of formula (I) obtained according to the claimed process can then be further processed according to any of the methods known in the literature that involve use of such an intermediate to give the end desired contrast agents, such as iopamidol, iohexol, ioversol or iomeprol.

It is therefore a further specific object of the present invention a process for the manufacture of a product selected from the group consisting of iopamidol, iohexol, ioversol, and iomeprol involving the use of a corresponding intermediate compound of formula (I), said process being characterised in that the intermediate of formula (I) is obtained by direct amidation of a dialkyl ester of 5-amino-1,3-benzenedicarboxylic acid of formula (V),

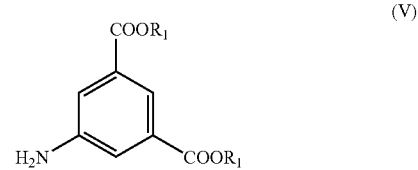
(V)

wherein $R_1$ represents a straight or branched ($C_1$-$C_4$)-alkyl group, with at least the stoichiometric amount of an amine of formula $H_2NR$ wherein R is a 1,3-dihydroxy-2-propyl or a 2,3-dihydroxy-1-propyl group.

A further specific object of the invention is, in particular, a process for the preparation of iopamidol which comprises
manufacturing an intermediate of formula (I) wherein R is a 1,3-dihydroxy-2-propyl group by the new process of the present invention;
suitably iodinating the benzene ring; and
introducing the (S)-2-(acetyloxy)propanoyl group on the 5-amino group.

Another further specific object of the invention is, in particular, a process for the preparation of iohekol which comprises
manufacturing an intermediate of formula (I) wherein R is a 2,3-dihydroxy-1-propyl group by the new process of the present invention;
suitably iodinating the benzene ring; and
N-acetylating and suitably N-alkylating the 5-amino group.

The following examples further illustrate the present invention but need not to be viewed as a limitation to the scope thereof.

EXAMPLE 1

5-amino-N,N'-bis[2-hydroxy-1-(hydroxymethyl)ethyl]-1,3-benzenedicarboxamide

5-Amino-1,3-benzenedicarboxylic acid dimethyl ester (40.0 g, 191 mmol) and 2-amino-1,3-dihydroxypropane (104.5 g, 1.147 mol) are loaded into a 1 L vessel equipped with a mechanical stirrer, a thermometer and a refluxing refrigerator. The suspension is heated up to 105° C., and is maintained at this temperature for 150 minutes to yield a solution. After cooling to 50° C., methanol (0.7 L) is added and the obtained suspension is maintained for 4 hours at room temperature. The solid that separates is filtered, washed with methanol (0.3 L), and dried in the oven at 45° C. for 4 hours yielding the compound of the title (56.3 g, 0.172 mol, yield: 90%).

EXAMPLE 2

5-amino-N,N'-bis[2-hydroxy-1-(hydroxymethyl)ethyl]-1,3-benzenedicarboxamide

2-Amino-1,3-dihydroxypropane (27.4 g, 300 mmol) and 1.5M solution of sodium methylate in methanol (14.3 mL, 21.5 mmol) are added to a suspension of 5-amino-1,3-benzenedicarboxylic acid dimethyl ester (30.0 g, 143 mmol) in methanol (0.2 L). The reaction mixture is heated to the reflux temperature to get a solution. After 2.5 hours of reflux and 4 hours at room temperature the reaction mixture is filtered and the solid on filter is washed with methanol (40 mL) and dried yielding the product of the title (43.5 g, 133 mmol, yield: 93%).

EXAMPLE 3

5-amino-N,N'-bis[2-hydroxy-1-(hydroxymethyl)ethyl]-1,3-benzenedicarboxamide

A mixture of 2-amino-1,3-dihydroxypropane (31 g, 340 mmol) and 5-amino-1,3-benzenedicarboxylic acid di-n-butyl ester (20.0 g, 68.2 mmol) is heated to 125° C. for 3 hours while the n-butyl alcohol which forms is distilled off. After cooling the reaction mixture to about 70° C. the solution is diluted with methanol (0.35 L) and a solid product crystallizes out. After 4 hours at room temperature the mixture is filtered and the solid on filter is washed with methanol (30 mL) and dried yielding the compound of the title (21.4 g, 65.5 mmol, yield: 96%).

EXAMPLE 4

5-amino-N,N'-bis[2-hydroxy-1-(hydroxymethyl)ethyl]-1,3-benzenedicarboxamide

5-Amino-1,3-benzenedicarboxylic acid di-n-butyl ester (1148 g, 3.91 mol) is loaded into a 10 L reaction vessel containing methanol (7.5 L) and a 1.5M solution of sodium methylate in methanol (0.39 L, 0.59 mol) and 2-amino-1,3-dihydroxypropane (820 g, 9.0 mol) are added thereto. The reaction mixture is then heated to the reflux temperature and kept at this temperature for 4 hours. The mixture is then concentrated to 4 L, cooled to 25° C. and after one night at room temperature it is filtered. The solid on filter is washed with methanol (2×1.3 L) and dried yielding the compound of the title (1215 g, 3.71 mol, yield: 95%).

EXAMPLE 5

5-amino-N,N'-bis(2,3-dihydroxy-1-propyl)-1,3-benzenedicarboxamide

The compound of the title is obtained by following substantially the same procedure as in the preceding example but using 1-amino-2,3-dihydroxypropane instead of 2-amino-1,3-dihydroxypropane.

EXAMPLE 6

Preparation of the 5-amino-1,3-benzenedicarboxylic Acid Dimethyl Ester

5-Nitro-1,3-benzenedicarboxylic acid dimethyl ester (95.7 g, 0.4 mol) and 5% Pd/C (8 g) are loaded into a 2 L hydrogenation vessel equipped with a thermometer and a mechanical stirrer, that contains methanol (0.8 L) and 2M HCl (0.3 L; 0.6 mol). The obtained suspension is maintained under mechanical stirring and purged with nitrogen washings, at the end of which the hydrogenation reaction is carried out at a temperature comprised between 45 and 55° C. The reaction is complete in 2 hours. A nitrogen flow is then passed through the reaction vessel to wash out any hydrogen gas, the catalyst is filtered off and the obtained solution is evaporated under vacuum to yield a solid residue. The obtained product is loaded into a 5 L vessel, equipped with a mechanical stirrer, and containing deionized water (3 L) and 34% HCl (0.1 L). The obtained suspension is filtered from the insoluble residue and 2M NaOH is added to the filtrate up to pH 10. The solid product that crystallizes out is recovered by filtration, washed with deionized water and dried under vacuum in the presence of $P_2O_5$ yielding the compound of the title (77.0 g; 0.368 mol, yield: 92%).

The $^1$H-NMR, $^{13}$C-NMR, IR and MS are consistent with the indicated structure

EXAMPLE 7

Preparation of 5-amino-1,3-benzenedicarboxylic acid di-n-butyl Ester

A mixture of 5-amino-1,3-benzenedicarboxylic acid (632 g, 3.49 mol), n-butyl alcohol (7.5 L) and p-toluenesulphonic acid (860 g, 4.52 mol) is loaded into a 10 L reaction vessel and heated to 97° C. under stirring under a reduced pressure of about 450 mBar removing the azeotrope n-butyl alcohol/water that forms. After 11 hours of heating the reaction mixture is concentrated to 2.4 L, cooled to 60° C. and neutralised by the addition of 5M NaOH (0.9 L). The mixture is further cooled to about 10° C. and diluted with water 3.4 L). After 15 hours at room temperature the solid is recovered by filtration, washed with water (2×1 L) and dried yielding the 5-amino-1,3-benzenedicarboxylic acid di-n-butyl ester (930 g, 3.17 mol, yield: 91%).

EXAMPLE 8

Preparation of Iopamidol a) 5-amino-N,N'-bis[2-hydroxy-1-(hydroxymethyl)ethyl]-2,4,6-triiodo-1,3-benzenedicarboxamide The compound of Example 1 (9.0 g, 27.5 mmol), deionized water (0.75 L) and 1M HCl (15 mL) are loaded into a 1 L vessel, equipped with a mechanical stirrer and a thermometer. A solution of $NaICl_2$ (sol. at 25.6% of iodine) (38.6 g, 0.078 mol) is added thereto in 15 minutes and the obtained solution is maintained under stirring for 30 minutes at room temperature and at 50° C. for 5 hours.

The solid product which precipitates is filtered, washed with a solution of sodium bisulfite, then with deionized water and dried under vacuum in a oven yielding the 5-amino-N,N'-bis[2-hydroxy-1-(hydroxymethyl)ethyl]-2,4,6-triiodo-1,3-benzenedicarboxamide intermediate (14.5 g, 20.6 mmol, yield: 75%).

The $^1$H-NMR, $^{13}$C-NMR, IR and MS are consistent with the indicated structure.

b) Iopamidol

The 5-amino-N,N'-bis[2-hydroxy-1-(hydroxymethyl)ethyl]-2,4,6-triiodo-1,3-benzenedicarboxamide intermediate product obtained by following the procedure of step a) above (21 g, 29.8 mmol) is added to N,N-dimethylacetamide (0.2 L) and anhydrous HCl (0.33 g; 9 mmol) is bubbled therein. The solution is then cooled to 15° C. and (S)-2-(acetyloxy)propanoyl chloride (31.4 g, 208 mmol) is then dripped therein in two hours. The mixture is stirred for 48 hours at 23° C., the solvent is partially evaporated and the residue is taken up with deionized water (0.2 L). The solution is warmed to the temperature of 55° C. and kept at this temperature for 2 hours, to hydrolyse the obtained oxazolidine compounds having the structure indicated below.

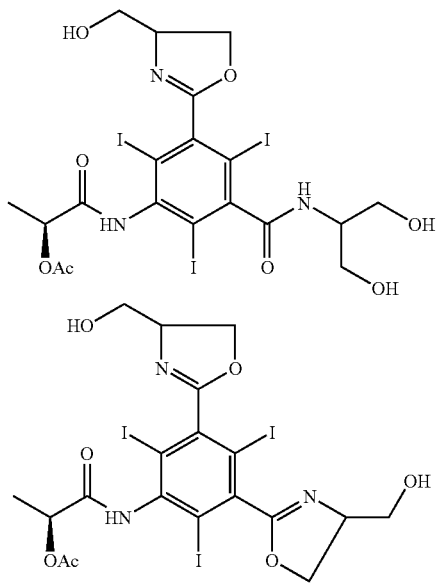

After cooling to 40° C., 2M NaOH is added until the pH of the mixture reaches 10.5 and this pH value is maintained up to the complete hydrolysis of the acetic group.

The reaction mixture cooled to 25° C., is then loaded into a system of ion exchange resin columns, cationic and anionic respectively. The eluate is collected, and concentrated to a residue which is then crystallized from ethanol. The solid is filtered, washed on filter with ethanol and dried at a temperature of 45° C. for 5 hours in an oven yielding the desired iopamidol (17.8 g, 22.9 mmol, yield: 77%).

The $^1$H-NMR, $^{13}$C-NMR, IR and MS are consistent with the indicated structure.

EXAMPLE 9

Preparation of Iopamidol

Iopamidol can also be prepared by the above procedure where the first step, the preparation of 5-amino-N,N'-bis[2-hydroxy-1-(hydroxymethyl)ethyl]-2,4,6-triiodo-1,3-benzenedicarboxamide is carried out as follows:

The compound of Example 1 (671 g, 2.05 mol), is loaded into a 10 L reaction vessel containing deionized water (9.2 L) and 96% $H_2SO_4$ (107 g) and the solution is heated to 70° C. ICl (a solution of 44% iodine in 14.5% HCl) (1920 g, 6.65 mol) is gradually dripped in (about 1 hour) and the reaction mixture is then maintained at about 70° C. for additional 9 hours. After overnight at room temperature the solid is recovered by filtration, washed on filter with water (2×0.6 L), and dried yielding the 5-amino-N,N'-bis[2-hydroxy-1-(hydroxymethyl)ethyl]-2,4,6-triiodo-1,3-benzenedicarboxamide (1300 g, 1.85 mol, yield: 90%).

EXAMPLE 10

Preparation of Iohexol a) 5-(acetylamino)-N,N'-bis(2,3-dihydroxypropyl)-2,4,6-triiodo-1,3-benzenedicarboxamide 5-Amino-N,N'-bis[2,3-dihydroxypropyl]-1,3-benzenedicarboxamide (44 g, 62 mmol) is suspended in acetic anhydride (210 mL) and concentrated sulphuric acid (1.5 mL) is added thereto. The reaction mixture is then warmed to 60° C. for 90 minutes, concentrated and the obtained residue is taken up with a mixture of methanol (120 mL) and deionized water (70 mL) and heated to 50° C. while the pH is kept at 10.5 by sequential additions of NaOH.

Once the hydrolysis reaction is over, the solution is cooled to room temperature and neutralised with HCl.

The obtained solution is stirred at room temperature for 18 hours, then the solid that precipitates is recovered by filtration, washed with water and dried yielding the intermediate 5-(acetylamino)-N,N'-bis(2,3-dihydroxypropyl)-2,4,6-triiodo-1,3-benzenedicarboxamide (32.0 g, 43 mmol, yield: 69%).

b) Iohexol

A sample of the above prepared product (30 g, 40 mmol) is dissolved in propylene glycol (100 mL) with the addition of 4M sodium methylate (15 mL, 60 mmol) and brought at a temperature of 50° C. The obtained solution is partially concentrated and cooled to room temperature. 1-Chloro-2,3-dihydroxypropane (5.0 mL, 60 mmol) is then added thereto, the reaction mixture is then maintained under stirring for 32 hours, and concentrated under vacuum to a solid residue which is taken up with methanol and filtered. The filtrate is concentrated to a residue, that is dissolved in water and purified from salts by means of ionic exchange resins. The deionized solution is concentrated to a residue and the obtained product is crystallized from butanol, thus yielding upon filtration and drying the desired iohexol (19.7 g, 24 mmol, yield: 60%).

The $^1$H-NMR, $^{13}$C-NMR, IR and MS are consistent with the indicated structure.

What is claimed is:

1. A process for the preparation of a compound of formula (I)

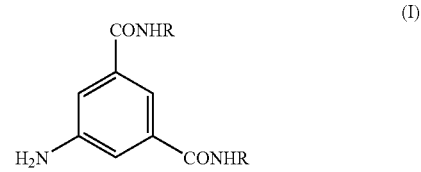

wherein R represents a 2,3-dihydroxy-1-propyl or a 1,3-dihydroxy-2-propyl radical, which comprises reacting a di-alkyl ester of 5-amino-1,3-benzenedicarboxylic acid of formula (V),

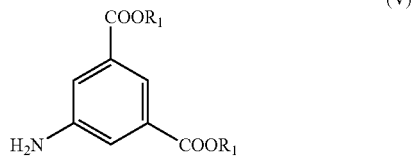

(V)

wherein $R_1$ represents a straight or branched $(C_1$-$C_4)$-alkyl group, with at least two moles of an amine of formula $H_2NR$ wherein R is as defined above.

2. The process of claim 1 wherein the starting compound of formula (V) is obtained by reduction of the corresponding 5-nitro-1,3-benzenedicarboxylic acid di-alkyl esters of formula (VI),

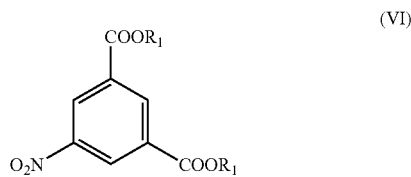

(VI)

wherein $R_1$ is as defined above.

3. The process of claim 1 wherein the starting compound of formula (V) is obtained by esterification of the 5-amino-1,3-benzenedicarboxylic acid with an alcohol $R^1OH$.

4. The process of claim 1 wherein the reaction is carried out at a temperature of from about 65° C. to about 150° C., using an excess of the amine $RNH_2$ with respect to the stoichiometric amount required by the reaction, either in the presence of an organic solvent, selected from $C_1$-$C_6$ straight or branched alkanols, $C_1$-$C_4$ straight or branched alkoxy-$C_2$-$C_4$ straight or branched alkanols, $C_1$-$C_4$ straight or branched alkyl ethers and dipolar aprotic organic solvents or in the absence of a separate organic solvent, using the excess of the amine in its molten state as the reaction medium.

5. The process of claim 4 wherein the reaction is carried out in the presence of an organic solvent and of a strong basic catalyst.

6. The process of claim 5 wherein the-organic solvent is selected from $C_1$-$C_4$ straight or branched alkanols, and $C_1$-$C_4$ straight alkoxy-$C_2$-$C_4$ straight alkanols, and the strong basic catalyst is an alkali metal $C_1$-$C_4$ straight or branched aliphatic alcoholate.

7. The process of claim 2 wherein the compound of formula (V) is not isolated.

8. The process of claim 1 wherein $R_1$ is a n-butyl group.

9. A process for the manufacture of a product selected from the group consisting of iopamidol, iohexol, ioversol, and iomeprol involving the use of a corresponding intermediate compound of formula (I), said process being characterised in that the intermediate of formula (I) is obtained by the process of any of the preceding claims 1 to 8.

10. A process for the preparation of iopamidol which process comprises
preparing manufacturing an intermediate of formula (I) wherein R is a 1,3-dihydroxy-2-propyl group by the process of any of preceding claims 1 to 8;
suitably iodinating the benzene ring; and
introducing the (S)-2-(acetyloxy)propanoyl group on the 5-amino group.

11. A process for the preparation of iohexol which process comprises
preparing an intermediate of formula (I) wherein R is a 2,3-dihydroxy-1-propyl group by the process of any of preceding claims 1 to 8;
suitably iodinating the benzene ring; and
N-acetylating and suitably N-alkylating the 5-amino group.

12. The process of claim 3 wherein the compound of formula (V) is not isolated.

13. A process for the manufacture of a product selected from the group consisting of iopamidol, iohexol, ioversol, and iomeprol involving the use of a corresponding intermediate compound of formula (I), said process being characterised in that the intermediate of formula (I) is obtained by the process of claim 12.

14. A process for the preparation of iopamidol which process comprises
preparing manufacturing an intermediate of formula (I) wherein R is a 1,3-dihydroxy-2-propyl group by the process of claim 12;
suitably iodinating the benzene ring; and
introducing the (S)-2-(acetyloxy)propanoyl group on the 5-amino group.

15. A process for the preparation of iohexol which process comprises
preparing an intermediate of formula (I) wherein R is a 2,3-dihydroxy-1-propyl group by the process of claim 12;
suitably iodinating the benzene ring; and
N-acetylating and suitably N-alkylating the 5-amino group.

* * * * *